United States Patent [19]

Olsson

[11] Patent Number: 5,073,540

[45] Date of Patent: Dec. 17, 1991

[54] COMPOSITE BINDING SITE DRUGS

[75] Inventor: Lennart Olsson, Orinda, Calif.

[73] Assignee: Receptron, Concord, Calif.

[21] Appl. No.: 351,764

[22] Filed: May 15, 1989

[51] Int. Cl.$^5$ .................... C07K 7/40; A61K 37/26; A61K 37/02

[52] U.S. Cl. .......................................... 514/3; 514/8; 530/303

[58] Field of Search ................ 530/405, 303; 514/3, 514/8

[56] References Cited

U.S. PATENT DOCUMENTS 4,478,823  10/1984  Sanderson ........................... 424/88
4,761,371  8/1988  Bell et al. ........................... 435/69.1

OTHER PUBLICATIONS

Watts et al., Journal of Immunology, vol. 139, 3878-3885, No. 11, 12/01/87 Lenninger Biochemistry, 2nd Edition, p. 109, 1978.

"The Human Insulin Receptor cDNA: The Structural Basis for Hormone-Activated Transmembrane Signalling," by Ebina et al., in *Cell* (1985), 40:747-758.

"Human Insulin Receptor and Its Relationship to the Tyrosine Kinase Family of Oncogenes," by Ullrich et al., in *Nature* (1985), 313:756-761.

"Interaction Between Major Histocompatibility Complex Antigens and Epidermal Growth Factor Receptors on Human Cells" by Schreiber et al. in *The Journal of Cell Biology* (1984), 98:725-731.

"Human Epidermal Growth Factor Receptor cDNA Sequence and Aberrant Expression of the Amplified Gene in A431 Epidermoid Carcinoma Cells," by Ullrich et al., in *Nature* (1984), 309:418-425.

"The Original Function of MHC Antigens as the General Plasma Membrane Anchorage Site of Organogenesis-Directing Proteins," by S. Ohno in *Immunol. Rev.* (1977), 33:59-69.

"Possible Roles of Compound Membrane Receptors in the Immune System" by Simonsen and Olsson in *Ann. Immunol.* (1983), 134(d):85-92.

"Molecular Association Between Major Histocompatibility Complex Class I Antigens and Insulin Receptors in Mouse Liver Membranes" by Fehlmann et al. in *Proc. Natl. Acad. Sci. USA* (1985), 82:8634-8637.

"The Structure of Insulin Receptor and Its Subunits" by Kasuga et al. in *The Journal of Biological Chemistry* (1982), 257:10392-10399.

"The Major Histocompatibility Complex Class I Heavy Chain as a Structural Subunit of the Human Cell Membrane Insulin Receptor: Implications for the Range of Biological Functions of Histocompatibility Antigens:" by Due et al. in *Proc. Natl. Acad. Sci. USA* (1986), 83:6007-6011.

"Class I Histocompatibility Antigens and Insulin Receptors: Evidence for Interactions" by Phillips et al. in *Proc. Natl. Acad. Sci. USA* (1986), 83:3474-3478.

"Cross-Linking of Insulin Receptors to MHC Antigens in Human B Lymphocytes: Evidence for Selective Molecular Interactions" by Samson et al. in *The Journal of Immunology* (1986), 137(7):2293-2298.

*Primary Examiner*—Margaret Moskowitz
*Assistant Examiner*—Lila Feisee
*Attorney, Agent, or Firm*—Bertram I. Rowland

[57] ABSTRACT

Methods and compositions are provided for regulating surface membrane receptor response by providing novel proteinaceous compositions to bind to two separate sites of a surface membrane receptor, the binding site of the receptor and an allosteric site, which binds to a sequence of a Class I MHC antigen. The resulting products may act as agonist or antagonist to the normal function of the receptor and find use in the control of physiological processes.

6 Claims, No Drawings

COMPOSITE BINDING SITE DRUGS

INTRODUCTION

1. Technical Field

The field of the subject invention concerns therapies associated with ligand activated surface membrane receptors.

2. Background

Cells communicate and are regulated by a variety of compounds produced by the same or different cells. Cells have surface membrane receptors for binding to many of these compounds, which results in the transduction of a signal into the cytoplasm or nucleus. The membrane receptor serve a wide variety of purposes in the regulation of the cell, initiating mytosis, synthesis of nucleic acid, production of compounds which in turn which may be secreted and act on other cells, and the like.

A large number of proteins have been shown to bind to surface membrane receptors and initiate a cascade of events. Proteins which interact with surface membrane receptors include interferons, growth factors, such as epidermal growth factor, platelet derived growth factor, transforming growth factor, both $\alpha$- and $\beta$-neuronal growth factor, colony stimulating factors, such as granulocyte- and monocyte-colony stimulating factor, blast stimulating factor-E, and the like; major histocompatibility complex antigens, insulin receptor, asialoglycoprotein receptor, low density lipoprotein receptor, and the like.

Many of these receptors share common domains, involving a cytoplasmic domain, which in many cases has tyrosine kinase activity, transmembrane integrator sequence, and an extracellular domain which provides the binding site for the ligand. Furthermore, in many cases, the complex of the surface membrane receptor and the ligand is internalized, where the receptor is recycled to the surface without the ligand. The binding of the ligand therefore results in a transduced signal, the complex of the ligand and receptor is then endocytosed or internalized, where the ligand is removed from the receptor and the receptor is recycled to the surface for binding to ligand. In this way, high affinity receptors interact with low concentrations of complementary ligand and be continuously replenished by mechanisms other than the separation of the ligand and the receptor by dissolution.

There are many diseases associated with aberrant behavior of a receptor or the ligand. In the case of some diabetics, substantially reduced concentrations of insulin result in reduced glucose uptake, which results in numerous deleterious indications of diabetes. It would therefore be of interest to be able to provide more effective therapies for diseases associated with the first membrane receptors.

Relevant Literature

Ebina, et al., Cell (1985) 40:747-758 and Ullrich, et al., Nature (1985) 313:756-761 describe the insulin receptor, its amino acid sequence and functioning domains. Ullrich, et al., Nature (1984) 309:418-425 describe the EGF receptor and its relation to other growth factor receptors, as well oncogenes.

For a review of biological functions of MHC Class I antigens see Ohno, Immunol. Rev. (1977) 33:59-69; and Simonsen, Prog. Allergy (1985) 36:151-176. For a description of the insulin receptor see Cuatrecasas, Biol. Chem. (1972) 247:1980-1991; Kasuga, et al., ibid. (1982) 257:10392-10399; and Kasuga, et al., ibid. (1983) 258:10973-10980. For suggestion that Class I antigens and insulin receptors interact, see Olsson, In Cell Fusion: Gene Transfer and Transformation (eds. Beers & Bassett) 395-403 (Raven Press, New York, 1984); Simonsen and Olsson, Ann. Immunol. (1983) 134D:85-92.

Other evidence supporting the interaction between MHC products and insulin receptor may be found in Fehlman et al Proc. Natl. Acad. Sci. U.S.A. (1985) 82:8634-8637; Philips, et al., ibid. (1986) 83:3474-3478; Due, et al., ibid. (1986) 83:6007-6011, and Samson, et al., J. Immunology (1986) 137:2293-2298.

SUMMARY OF THE INVENTION

Compositions are provided for modulating activity of cell surface receptors, by employing protein compositions comprising a sequence binding to the binding site of a surface membrane receptor and a sequence from a Class I major histocompatibility complex antigen, which binds to the same receptor. By employing a combination of the two domains joined together, a product having high affinity for the receptor is achieved, where by appropriate choice of the sequence which binds to the binding site of the receptor, agonist or antagonist activity may be achieved.

DESCRIPTION OF THE SPECIFIC EMBODIMENTS

Novel proteinaceous compositions are provided comprising a sequence capable of binding to the binding site of a surface membrane receptor and a sequence of a major histocompatibility complex (MHC) antigen, particularly the polymorphic region of a Class I HLA—B or —C antigen. The two sequences may be joined by any convenient linking means which allows for the sequences to bind to their respective binding sites of the surface membrane receptor. Resulting compositions provide for high affinity binding to the receptor and depending upon the nature of the sequence of the complementary ligand may serve as agonists or antagonists of the function of the ligand activating or inhibiting the action of the receptor.

A large number of mammalian, particularly human, surface membrane proteins are involved with transduction of signals and serve as receptors for a wide variety of ligands. For the most part, receptors are defined by the ligand which activates the receptor for transduction or serves to endocytose the ligand. These receptors include endocrine, paracrine and autocrine receptors, adrenergic receptors, lipoprotein receptors, opiate receptors, and steroid receptors. These receptors include surface membrane receptors for asialoglycoprotein, insulin, somatostatin, somatotropins; for growth factors, such as growth hormone, platelet derived growth factor, insulin like growth factor, epidermal growth factor, $\alpha$-transforming growth factor, nerve growth factor, fibroblast growth factor, somatomedin, vasopressin, prostaglandins, eosinophil chemotactic factor, acetylcholine, thyroxine stimulating hormone (TSH), epinephrine; endorphins, enkephalins and dynorphin; neurotensin, oxytocin, transferrin, substance P, lymphokines, such as 1-, 2-, 3-, and 4-, 5-, 6- and 7, etc.; colony stimulating factors, such as GM-CSF, M-CSF, E-CSF, etc.; lipoproteins, such as low density lipoprotein; steroids, such as estrogen, androgen, glucocorticoids, corticosteroids, etc. Of particular interest are receptors which are cycled, that is, internalized into the cytoplasm and then returned to the plasma membrane surface. Illustrative of these receptors are the receptors for insulin, EGF, LDL, transferrin, interleukins, and asialoglycoprotein.

Many of the surface membrane receptors also have kinase activity, particularly tyrosine kinase activity. For example, with the insulin receptor, it is found that an MHC antigen sequence results in reduction of the tyrosine kinase activity.

Instead of using a sequence of the natural ligand, other sequences may be employed which specifically bind to the binding site of the membrane receptor. For example, antibodies may be employed which are specific for the binding site, because they specifically bind to a sequence of the membrane receptor, blocking binding to the membrane receptor or of a paratope which mimics the sequence of the ligand which binds to the binding site of the membrane receptor. Thus, the sequence which is employed may be varied widely, so long as it has a significant affinity for the binding of the receptor and may act as an agonist or antagonist(s) transduced by the receptor when bound to complementary ligand.

The sequence employed will be of at least about 6 amino acids, usually at least 8 amino acids, and as already indicated, may be the entire natural ligand or a subunit thereof. Thus, the molecular weight of the ligand portion of the molecule will usually be under about 500 kD, usually under about 200 kD and preferably under about 100 kD. Preferably, the sequence will be fewer than 200 amino acids, usually fewer than 100 amino acids, more usually fewer than 60 amino acids. For synthetic ligands, the number of amino acids will preferably be fewer than 60 amino acids, more preferably fewer than 35 amino acids.

Ligands of particular interest are indicated above in the list of receptors and include insulin, asialoglycoprotein, low density lipoprotein, epidermal growth factor, transferrin, interleukins, and other ligands which bind to receptors which also bind to the sequences allosterically resulting in a change in their signal transduction.

In those situations where non-peptide compounds have been found to compete with epitopes of ligands, these compounds may be used in place of a peptide sequence.

The other portion of the molecule will be based upon sequences associated with the polymorphic regions of human MHC Class I antigens, particularly —B and —C, and their animal analogs. Particular interest are the $\alpha_1$- and $\alpha_2$- domains, more particularly the $\alpha_1$-domain.

The entire MHC antigen may be employed to provide the desired sequence or only a portion thereof, preferably only a portion thereof. Since the $\alpha_1$-subunit is the only subunit that has the polymorphic region, normally only the $\alpha_1$- subunit or fragment thereof will be employed.

Of particular interest are the amino acid sequences of at least about 8 amino acids involved in the polymorphic regions of $\alpha_1$ and $\alpha_2$, ranging from amino acid 50 to amino acid 90, more particularly amino acids 55 to 90, usually 60 to 90, more particularly 65 to 90 or 90 to 120, more usually 90 to 116, where the amino acid sequences of interest are usually in the C-terminus of the $\alpha_1$-domain and N-terminus of the $\alpha_2$-domain. The region 60–85, more particularly 65 to 85 or 70 to 85 are found to be of particular interest.

It is found that the amino acids from 83 to 84, more particularly 83 to 85, may be of particular interest. For both MHC Class I D and K, or the analogous HLA-B or -C, the sequence is R Y or R Y Y.

Peptides of particular interest will comprise this sequence and may include at least about 20, usually at least about 15, and preferably not more than about 10 amino acids on either side of the sequence, preferably having at least 5 amino acids at the N-terminal side, and more preferably not having more than about 5-amino acids at the C-terminal side. The presence of two tyrosines is particularly desirable for the insulin receptor.

Desirably, the total number of amino acids will not exceed 20, preferably not exceed about 18, more preferably not exceed about 15 within the sequences indicated above, and may be as few as 8, more usually at least about 10.

Also of interest is the region from about amino acid 30 to amino acid 45, more particularly 32 to 40, particularly an oligopeptide of at least four amino acids, more usually at least about six amino acids, and preferably at least about eight amino acids, where the sequence includes a tetramer involving an acidic amino acid and a basic amino acid separated by one neutral amino acid, particularly a neutral amino acid of at least five carbon atoms and one of the acidic or basic amino acids is flanked by a neutral amino acid. Of particular interest is where the intervening neutral amino acid is an aromatic or aliphatic hydrocarbon amino acid, e.g. glycine or phenylalanine.

As with the ligand, antibodies may also find use for binding to the allosteric site of the membrane receptor. Thus, antibodies may be prepared which specifically bind to such allosteric site and act as antagonist or agonist for the MHC Class I antigen effect.

Alternatively, one may employ monoclonal antibodies specific for the $\alpha_1$-domain to be used as immunogens for the production of anti-idiotype antibodies, which will mimic the conformation of the Class I antigen epitope to which the monoclonal antibody binds. Thus, the anti-idiotype may act as a substitute Class I antigen and may serve to block autoimmunity. The whole antibodies need not be employed, the variable region sufficing, or larger fragments such as Fab, F(ab')$_2$, Fab', etc.

The antibodies may be prepared in accordance with conventional ways. Particularly, the Class I antigen may be used as an immunogen and injected into an appropriate host, conveniently a mouse, for initiating an immune response. One or more booster injections may be employed at two or more week intervals. Two to three days after the last injection, the animal host may be sacrificed, the spleen isolated, and the B-lymphocytes immortalized. Various techniques exist for immortalization, conveniently fusion with a myeloid cell, followed by selecting for hybridomas and screening, under limiting dilution conditions, for hybridomas producing antibodies having the desired characteristics. Thus, in the present situation, the Class I antigen could be used for screening or the antibody to the domain of interest, in the case of the anti-idiotype.

Instead of employing antibodies, oligopeptides may be employed which are capable of mimicking the site of the Class I antigen associated with binding to the receptor or the receptor site which binds to the Class I antigen. Thus, by preparing oligopeptides having a sequence substantially conforming to a sequence of the binding domain of the Class I antigen, or active fragment thereof, one can substitute for the presence of the Class I antigen by using the oligopeptide for activation of the receptor. By modifying the sequence, for example by substitutions, deletions or insertions, where usually from 1 to 3, usually from 1 to 2, amino acids are involved, enhanced binding of the peptide to the receptor may be achieved.

By non-conservative substitutions are intended those substitutions which substantially differ as to polarity and/or size, where each of the lines in the following table indicates what are conservative substitutions.

TABLE A

| | |
|---|---|
| Neutral Aliphatic Non-polar | |
| small | G, A (P) |
| large | V, I, L |
| Polar | |
| Oxy or Thio | S, T, C, M |
| Amide | N, Q |
| Aromatic | F, W, H, Y |
| Charged | |
| Acidic | D, E |
| Basic | K, R |

( ) intends that the amino acid will normally not be used as a substitute for others on the same line.

Depending upon the selection of the sequence for binding to the binding site and the allosteric site, various different types of linking groups may be employed. The linking groups may be simply a bond, particularly where at least 50% of the native molecule or subunit is employed. Alternatively, linking groups may involve polypeptide or non-polypeptide linkers. The polypeptide linkers will be selective so as to allow for sufficient flexibility for binding of the two binding sequences to the membrane receptor. For peptide bridges, usually, the amino acid linking group will have at least one amino acid, not more than about 30 amino acids, usually not more than about 20 amino acids. The number of amino acids is limited by the effect of the number on the ability of the two sequences to bind simultaneously to the receptor. Instead of polypeptide, one could use a bifunctional group which links to amino, hydroxyl or thiol groups which are present in the sequences. Thus, linkers may employ carboxyl groups, carbonyl groups, particularly aldehydes, under reducing conditions, activated olefins, e.g., maleimide, activated halides or pseudohalides, such as benzyl halides or superhalides, or the like. Another alternative is mono- and polysaccharides having from 1 to 20, usually 1 to 6 sugars, generally of from 5 to 6 carbon atoms, where the sugars may include carboxy, amino and thiol groups.

Usually the linking group will have at least one atom other than hydrogen and not more than about 60 atoms other than hydrogen, usually not more than 40 atoms other than hydrogen, with a chain of from about 1 to 30 atoms, more usually from about 2 to 20 atoms. The linking group may be aliphatic, alicyclic, aromatic, or heterocyclic, preferably aliphatic and more preferably having from about 1 to 10, usually from about 1 to 6 heteroatoms, which may be nitrogen, oxygen, sulfur, phosphorous, or the like, while with sugars the heteroatoms may be as high as 50, usually not more than about 30.

A wide variety of compounds are generally available for linking polypeptides, such as glutaraldehyde, N-succinimidyl p-maleimidobenzoate methyldithioacetic acid, p-diazobenzoic acid, etc. Preferably, the linking group will have two different functionalities for linking to the polypeptide sequences, where the linking may occur sequentially.

After linking of the two groups, the composition may be purified by chromatography, solvent extraction, affinity chromatography, dialysis, electrophoresis, or the like. As appropriate, the product may be analyzed to ensure that the desired product has been obtained.

Instead of joining two sequences synthetically, the sequences may be prepared by synthetic means, where the peptide will generally vary from about 20 to 80, more usually from about 30 to 60 amino acids. Automatic devices exist for synthesizing polypeptides of 60 amino acids or greater with high efficiency, where the amino acids are added sequentially, where functionalities uninvolved in the bonding are protected. After each addition, the terminal amino or carboxy group is deprotected and then may be used as the site of addition of the next amino acid. Conveniently, the first amino acid is joined through a linking group to a solid support, where after completion of the synthesis of the desired polypeptide, remaining protective groups bonded to the side chain functional groups may be removed and the resulting polypeptide cleaved from the support.

Also, recombinant techniques may be employed, which will be particularly advantageous where twenty percent or more of the protein or subunit of interest is employed in the product. In this case, the gene for the subunit of the ligand or MHC antigen or fragment thereof may be joined in appropriate order, either directly through an adapter to provide an open reading frame encoding the allosteric binding sequence and the receptor binding sequence. The resulting fused gene may then be inserted into an appropriate expression vector, comprising transcriptional and translational initiation and termination regulatory regions, which are separated by one or more convenient restriction sites for insertion of the gene. The resulting expression cassette will usually be inserted into a vector which comprises a replication system functional in the expression host and a marker for selection of transformants.

In some instances, integration is desired and the functional replication system may or may not be present. If desired, the gene may be modified by providing at the 5'-terminus in the direction of transcription a signal sequence which provides for secretion of the gene into the periplasmic space with certain prokaryotes or into the nutrient medium with other prokaryotes and eukaryotes. The transformants may then be grown in an appropriate medium, which may or may not employ the selective agent, and the product which is produced is harvested. Where the product is retained in the host, cells may be harvested, lysed and the protein product purified in accordance with conventional ways, e.g., chromatography, affinity chromatography, electrophoresis, or the like. Where the product is secreted into the supernatant, the supernatant may be continuously withdrawn and the product extracted and purified as described above.

The oligopeptide may be joined to other peptides for a variety of purposes. The oligopeptide may be linked through a variety of bifunctional agents, such as maleimidobenzoic, methyldithioacetic acid, mercaptobenzoic acid, S-pyridyl dithiopropionate, etc. The oligopeptides may be linked to proteins to provide immunogens for the production of antibodies. The oligopeptides may be linked, particularly by an intracellular cleavable linkage, to antibodies for site directed action. The oligopeptides may be linked to peptides to enhance stability, for site directed action, to provide additional physiological activity or the like. For conjugation techniques, see, for example, U.S. Pat. Nos. 3,817,837; 3,853,914; 3,850,752; 3,905,654; 4,156,081; 4,069,105; and 4,043,989, which are incorporated herein by reference.

As illustrative of the subject invention, the MHC Class I peptide $D^k$-(61-85) is joined at its N-terminus to the C-terminus of the B-chain of insulin or to the C-terminus of the A-chain in the absence of the B-chain of insulin. The $D^k$-(61-85) peptide may be joined directly or through a peptide chain of from about 5 to 10 amino acids. The product is readily prepared by employing the intact insulin gene and joining at its 3'-terminus a synthetic sequence encoding the $D^k$-(61-85) joined to the insulin gene by 15 to 30 glycines, which may be achieved by poly-G, C tailing, where the resulting product may have different lengths of the poly-glycine bridge. In this manner, one may fractionate the product and determine the specific length of bridge that is desired. Where the bridge length is significant, one can specifically synthesize the desired nucleotide length to produce the number of codons, providing for appropriate sequences joining to the insulin and MHC antigen gene to maintain the proper reading frame.

Of particular interest are oligopeptides comprising at least a portion of one of the following sequences, where the oligopeptides comprise as the active sequence, at least six amino acids, usually at least eight amino acids, more usually at least 12 amino acids, and fewer than 40 amino acids, more usually fewer than 30 amino acids, preferably, not more than about 25 amino acids, preferably being from about 8 to 25 amino acids, more preferably about 8 to 20 amino acids. It is understood that up to five, more usually up to about three substitutions or deletions may be made in the subject sequences, where the change will not be more than about 20 number %, usually not more than about 10 number % of the number of amino acids in the active sequence. Also the following sequences may be joined together either contiguously or by bridges of not more than about 20 amino acids, more usually not more than about 10 amino acids. Furthermore, where the sequences overlap, it is intended that the overlapping sequences not be repeated, but rather the non-overlapping sequences joined in proper sequence.

The oligopeptide will have at least six amino acids which are the same or substantially the same as a sequence included in the following sequence.

1. D T $aa^{32}$ F V R F D S D $aa^{40}$ $aa^{41}$
2. F V R F D S D $aa^{40}$ $aa^{41}$ S P R $aa^{45}$
3. W $aa^{52}$ E Q $aa^{55}$ $aa^{56}$ G P E Y W
4. W $aa^{61}$ $aa^{62}$ $aa^{63}$ T $aa^{65}$ $aa^{66}$ $aa^{67}$ K $aa^{69}$ $aa^{70}$ $aa^{71}$ Q
5. W $aa^{61}$ $aa^{62}$ $aa^{63}$ $aa^{64}$ $aa^{65}$ $aa^{66}$ $aa^{67}$ K $aa^{69}$ $aa^{70}$ $aa^{71}$ $aa^{72}$ $aa^{73}$ $aa^{74}$ $aa^{75}$ $aa^{76}$ $aa^{77}$ $aa^{78}$ $aa^{79}$ $aa^{80}$ $aa^{81}$ $aa^{82}$ $aa^{83}$ $aa^{84}$ $aa^{85}$
6. E Q $aa^{73}$ $aa^{74}$ R V $aa^{77}$ $aa^{78}$ R $aa^{80}$ $aa^{81}$ $aa^{82}$ R Y Y wherein:

$aa^{32}$ is any neutral aliphatic amino acid of from 4 to 6 carbon atoms particularly N, Q, V, I, or L, more particularly Q or L;

$aa^{40}$ is an aliphatic amino acid, charged or uncharged, usually non-polar or acidic of from 2 to 5, more usually 2 to 4 carbon atoms, particularly G, A, P, D or E, more particularly A or D;

$aa^{41}$ is an aliphatic amino acid, charged or uncharged of from 2 to 5, usually 3 t 5 carbon atoms, particularly G, A, P, S, T, D or E, more particularly A, T and E;

$aa^{44}$ is P, N, or Q, particularly P or Q;

$aa^{45}$ is any aliphatic amino acid, particularly G, A, S, T, M, K, R, or E, particularly G, E, or K;

$aa^{52}$ is a neutral aliphatic amino acid of from to 6 carbon atoms, particularly V, I, L or M, more particularly V or I;

$aa^{55}$ is any charged amino acid, particularly K, R, D, or E, more particularly K or E;

$aa^{56}$ is a charged amino acid, particularly D, E, K or R, more particularly E or K;

$aa^{61}$ is D or E;

$aa^{62}$ is K, R, G, or A, particularly R or G;

$aa^{63}$ is any aliphatic amino acid other than basic of from 4 to 6 carbon atoms, particularly D, E, I, L, V, N, or Q, more particularly E, N, or Q;

$aa^{64}$ is S, T, or M, particularly T;

$aa^{65}$ is any polar or basic amino acid of 4 to 6 carbon atoms, particularly N, Q, K or R, more particularly Q;

$aa^{66}$ is any aliphatic amino acid of from 4 to 6 carbon atoms, particularly L, I, V, K, R, N, or Q, more particularly K, I or N;

$aa^{67}$ is any neutral aliphatic or aromatic amino acid, particularly G, A, L, V, I, S, T, M, C F, Y, N, or Q, more particularly C, S, Y, or M;

$aa^{68}$ is K or R, particularly K;

$aa^{69}$ is any aliphatic neutral or acidic amino acid, particularly D, E, G, A, S, T, or M, particularly A or T;

$aa^{70}$ is any aliphatic amino acid, neutral, polar, or basic (other than acidic) from 3 to 6, usually 4 to 6 carbon atoms, particularly N, Q, K, R, S, or T, more particularly N, Q, or K;

$aa^{71}$ is any aliphatic amino acid other than basic, usually from 2 to 5 carbon atoms, particularly 20 G, A, S, T, D, or E, more particularly A or T;

$aa^{72}$ is N or Q, particularly Q;

$aa^{73}$ us S, T, F, Y, H, or W, particularly T;

$aa^{74}$ is D, E, F, Y, H, or W, particularly Y or D;

$aa^{75}$ is K or R, particularly R;

$aa^{76}$ is an aliphatic amino acid other than basic of from 4 to 6 carbon atoms, particularly D, E, V, I, or L, more particularly E or V;

$aa^{77}$ is a polar aliphatic amino acid of from 3 to 6 carbon atoms particularly N, Q, S, T, D, or E, more particularly N, D or S;

$aa^{78}$ is a non-polar aliphatic amino acid of from 3 to 6 carbon atoms, particularly A, P, V, I, or L, more particularly L;

$aa^{79}$ is K or R, particularly R;

$aa^{80}$ is a neutral aliphatic amino acid of from 3 to 6, usually 4 to 6 carbon atoms, particularly S, T, N,Q, I, V, or L, more particularly N, T, or I;

$aa^{81}$ is an aliphatic non-polar amino acid, particularly G, A, L, I, or V, more particularly A or L;

$aa^{82}$ is an aliphatic amino acid other than acidic, of from 2 to 6, usually 5 to 6, carbon atoms, particularly K, R, G, A, L, I, or V, more particularly L or R;

$aa^{83}$ is an aliphatic amino acid other than acidic of from 2 to 6 carbon atoms, particularly K, R, G, A, L, I, or V, more particularly G or R;

$aa^{84-85}$ are aromatic amino acids, particularly F, Y, H, or W, more particularly Y.

Preferably, there will usually not be more than three mutations in the above sequence as substitutions, deletions, or insertions.

Of particular interest is an amino acid sequence of at least 6, usually at least 8, amino acids coming within the following sequence.

W D/E R aa$^{63}$ T Q/R aa$^{66}$ aa$^{67}$ K aa$^{69}$ aa$^{70}$ aa$^{71}$ Q T/W aa$^{74}$ R V/E aa$^{77}$ L R aa$^{80}$ L/A L/R G/R Y Y wherein:
aa$^{63}$ is E, I, or N;
aa$^{66}$ is I, N, or K, particularly I;
aa$^{67}$ is A, C, S, M, or Y, particularly Y or C;
aa$^{69}$ is G, A, T, or P, particularly A or T;
aa$^{70}$ is Q, N, or K;
aa$^{71}$ is A, E, or T;
aa$^{74}$ is D, F, or Y, particularly D or Y;
aa$^{77}$ is N, S, or D;
aa$^{80}$ is I, N, or T.

where when two amino acids are indicated at a particular site, either amino acid may be employed interchangeably. Up to three of the amino acids may be subject to conservative or non-conservative changes, there being from 0 to 2 deletions or insertions of from 1 to 2 amino acids.

The oligopeptides may be used as ligands to determine the presence of particular receptors as a diagnostic. Thus, cells could be screened, intact or as a lysate, for the population of one or more receptors which bind the oligopeptide. The oligopeptides could be labeled, directly or indirectly, with a label which provides a detectable signal, e.g. radioisotope, fluorescers, enzyme, particle, chemiluminescer, etc. Thus, cells from tissue, e.g. biopsies, blood, or the like may be diagnosed in vitro or in vivo for the presence of receptors binding to the oligopeptides. In addition, the binding pattern with the MHC Class I antigen of various cells can be determined. Diseased states as a result of inadequate complexation between MHC Class I antigens and receptors can be determined. A large number of protocols are known and have been developed and appear in the patent and scientific literature. Commercially available assays include ELISA, EMIT, SLFIA, RIA, CEDIA, etc.

The oligopeptides may be employed in a variety of ways. For therapy, they may be administered parenterally, e.g. by injection at a particular site, for example, subcutaneously, intraperitoneally, intravascularly, or the like.

The formulations will usually involve a physiologically acceptable medium, such as deionized water, saline, aqueous ethanol, ethanol, phosphate buffered saline, and the like. Other additives may be included, such as buffers, stabilizers, other proteins, bacteriocides, or the like. The manner of formulation will vary depending upon the purpose of the formulation, the particular mode employed for modulating the receptor activity, the intended treatment, and the like. The formulation may involve capsules, liposomes, time delayed coatings, pills, or be formulated in pumps for continuous administration. Because of the wide variety of modes of treatment, the varying responses, the different disease states, or the like, no useful limits may be given for the concentration of the active components. These can be determined empirically in accordance with known ways. See, for example Harrison's, Principles of Internal Medicine, 11th ed. Braunwald, et al. ed, McGraw Hill Book Co., New York, 1987.

The subject compound may be used to enhance or reduce the physiological response of a mammalian cell as a result of binding to the receptor. The subject compositions are combined with the target cell in an appropriate nutrient medium, e.g., in a culture medium or in blood, when in vivo. For example, where the ligand sequence is insulin, enhanced glucose uptake is observed as compared to insulin.

The following examples are offered by way of illustration and not by way of limitation.

EXPERIMENTAL

Studies were performed with the 61-85 fragment of Dk antigen, (E-R-E-T-Q-I-A-K-G-N-E-Q-S-F-R-V-D-L-R-T-L-L-R-Y-Y) as well as the use of a number of controll peptides. Insulin activity was segregated into two factors, tyrosine kinase activity and glucose uptake.

Peptides

The two MHC Class I derived peptides D$^k$-(61-85), and K$^k$-(61-85) (differs by 63 is N, 73 is I, 77 is N and 81 is A) are both from the same region of the αl domain of the MHC Class I molecules (Klein, Natural history of the major histocompatibility complex (Wiley, New York)). Both peptides were synthesized by Applied Biosystems, Inc., (Foster City, CA), and quality controlled by mass spectrometry.

The D$^k$-(61-85) and K$^k$-(61-85) peptides were iodinated for some experiments using carrier-free Na$^{125}$I (Amersham) and iodobeads (Pierce) by incubating for 20 min., then purified by reversed-phase HPLC on a C$_{18}$ column (Beckman) in a linear 30-50% gradient of CH$_3$CN in 5 mM trifluoroacetic acid (TFA). The $^{125}$I-labeled peptide eluting first was stored at 4° C. in 50% CH$_3$CN/5 mM TFA. The labeled peptides were stable under these conditions for at least 3 months.

Control Peptides: ACTH-(1-24) (human), CCK-33 (porcine), dynorphin A (porcine), β-endorphin-(1-27) (camel), glucagon (human), and prosomatostatin-(1-32) (porcine) were all purchased from Peninsula Laboratories, Belmont, CA. The A-chain and B-chain of insulin (porcine) and glucagon-(1-21) (human) were obtained from Novo Industry, Denmark. ACTH-(1-24) was used as a routine control peptide.

Purified Insulin Receptor

The purified human IR and the cloned cytoplasmic kinase domain (IRKD) have been described (Ellis, et al. (1988) Virology 62:1634-39; Roth, et al. (1986) J. Biol. Chem. 261:3753-57). Briefly, the human IR was purified from placenta by immunoaffinity columns, using monoclonal antibodies and binding of IR with two heavy chains, each ∼130 kDa, and two light chains, each ∼90 kDa.

Tyrosine Kinase Activity

The cytoplasmic, cloned IRKD was constructed from the IR sequence (Ebena, et al. (1985) Cell 40:747-758; Ullrich, et. al. (1985) Nature 313:756-761) and expressed in insect cells by using a baculovirus expression vector. The domain is soluble (M$_r$∼48 kDa) and the kinase activity is constitutively expressed in vitro. The IRKD was purified to homogeneity by immunoaffinity chromatography.

The procedures to measure kinase activity of the purified IR and IRKD, and the effects of insulin have been described elsewhere (Roth, et al. (1986) supra). Briefly, 5.0 μl purified IR was mixed with 5.0 μl insulin (final concentration 1.0 μM), and buffer (50 mM HEPES, pH 7.6, 150 mM NaCl, 0.1% Triton X-100) added to a final volume of 20 μl. When peptide was used, it was added in 5.0 μl, the volume adjusted to 20 μl by adding buffer, and the mixture incubated (1 hr, 4° C.). After incubation, 10 μl of a solution containing 2.5 μCi $^{32}$P-labeled ATP (3,000 Ci/mmol; γ-labeled; Amersham), 50 mM HEPES, pH 7.6, 150 mM NaCl, 0.1% Triton X-100, 37.5 μM unlabeled ATP, 15 mM MgCl$_2$, and 6 MnCl$_2$ was added to a final volume of 30 μl. The mixture was then incubated for 30 min. at 24° C.

After incubation, 15 μl sample buffer was added, and the sample was boiled for 5 min., and run on 10% SDS-PAGE overnight. The gel was dried, and autoradiograms processed with an exposure time of 5-10 hr. For quantitative estimates the β-subunit band of IR and the IRKD bands were cut out and counted dry (Cerenkov) in a scintillation counter.

Substrate phosphorylation was done with poly([Glu,-Tyr];4:1) (Sigma) as substrate. The substrate was added to a final concentration of 1.0 mg/ml and the phosphorylation assay was conducted as described above. For quantitative estimates the entire lane from just below the insulin receptor band to a 20-kDa marker was cut out and counted or the substrate was precipitated with TCA. For the latter, 5 α$_1$ sample was dotted on to 3 MM paper (Whatman), washed 30 min. in ice cold 10% TCA, boiled 10 min. in 5% TCA, then washed twice in distilled water and twice in ethanol, and finally dried and counted.

Insulin Binding

Porcine monoiodinated [$^{125}$I]-insulin (iodinated at Tyr A14; 1,900-2,000 Ci/mmol) was obtained from NOVO Industry and Amersham. Unlabeled porcine insulin (NOVO) was dissolved in 10 mM HCl at 1 mM and stored immediately at −20° C.

The plate assay for insulin binding to its purified receptor has been described (Morgan and Roth (1985) Endocrinology 116, 1224-1226). Briefly, 50 μl of affinity-purified rabbit anti-mouse IgG (Jackson Immuno Research Lab., Inc., West Grove, Pa.) (40 μg/ml) in 20 mM NaHCO$_3$, pH 9.6, was added to 96-well polyvinyl chloride (PVC) plates. The plates were incubated (17-20 hrs, 4° C.), washed thrice in 50 mM HEPES, pH 7.8, with 150 mM NaCl, 0.1% Triton X-100, 0.05% BSA, and $2 \times 10^{-8}$ M monoclonal antibody (Amac, Inc., Westbrook, Me.) was added. After incubation (1 hr, 24° C.), the plates were washed, and insulin binding measured.

For binding measurements, $^{125}$I-insulin ($3 \times 10^{-10}$M) was added together with increasing amounts of unlabeled insulin, and incubated (90 min., 24° C.), washed, and the amount of free and bound $^{125}$I-labeled insulin measured. Bound insulin was determined by eluting IR off the plate with 0.1M HCl and measuring in a γ-counter. For data analysis, non-specific binding was defined as the amount bound in presence of $10^{-6}$M unlabeled insulin.

Results

The effect of D$^k$-(61-85) on both substrate (poly-[E,Y]) phosphorylation and IR autophosphorylation as a function of the peptide concentration, wherein IR tyrosine kinase activity is induced with $10^6$M insulin was determined. Both are strongly inhibited at a concentration of μM D$^k$-(61-85). The basal activity of IR (no insulin added) is inhibited 24-40% by D$^k$-(61-85) and K$^k$-(61-85). The effect of K$^k$-(61-85) is significantly weaker than D$^k$-(61-85) on autophosphoylation, with EC$_{50}$ values [95% confidence intervals] of 4.0 μM [2.2-7.2 μM] and 1.2 μM [0.3-2.2 μM] for K$^k$-(61-85) and D$^k$-(61-85), respectively, whereas no difference is observed in respect to substrate phosphorylation. None of the control peptides (e.g. ACTH-(1-24) are substrates for IR tyrosine kinase.

No significant depletion (degradation or adsorption), as examined by HPLC and $^{125}$I-labeled D$^k$-(61-65), K$^k$-(61-85), ACTH-(1-24), or dynorphin A is observed during the experimental period at concentrations above 0.1 μM. The D$^k$-(61-85) peptide does not affect IRKD phosphorylation, as demonstrated by pre-incubation of maximally autophosphorylated and $^{32}$P-labeled IR for 1 hr on ice with 10 μM peptide and subsequent incubation with 500 μM cold ATP for 0-60 min. at room temperature.

The D$^k$-(61-85) has no effect on the binding of insulin to IR. The EC$_{50}$ IR autophosphorylation is about $3 \times 10^{-9}$M insulin, corresponding approximately to K$_d$($2.8 \times 10^{-9}$M). D$^k$-(61-85), at 10 μM inhibits autophosphorylation at all insulin concentrations.

D$^k$-(61-85), 3 μM inhibits the insulin-induced IR autophosphorylation, but not the insulin receptor kinase domain phosphorylation, when IR and IRKD are used at comparable activities. IR is not a significant substrate for IRKD in the absence of insulin. IR becomes a significant substrate for IRKD when insulin is added. This observation is facilitated by the inhibitory effect of the peptide on IR autophosphorylation, because the IR phosphorylation as mediated by the tyrosine kinase of IR itself and the phosphorylation mediated by IRKD would otherwise be indistinguishable.

In the next study, the uptake of glucose in rat adipocytes was performed. Adipocytes are prepared from non-starved male rat epididymal fat pads (1.2-1.6 g fat per rat) by collagenase digestion. The buffered is KRH with 5% BSA: only plastic tubes are used. The digest is filtered (25 μl) washed and resuspended in approximately $4 \times$ the cell volume (estimated by lipocrit). An aliquot is removed for Coulter counting after staining with 2% osmiun tetroxide, filtration and dilution in saline. 50 μl of adipocyte suspension is added to the pre-incubation mix, 300 μl buffer, 50 μl insulin (80 nM) or buffer; 50 μl test solution (10×) or buffer and incubated for 30 min. at 37° C. in a shaking water bath. A blank without cells is included for background counting. D-[$^{14}$C]-glucose is subsequently added (about $10^5$dpm/sample) and incubation continued for 60 min. The incubation is terminated by layering the 400 μl sample on top of silicone oil, followed by a 30 sec. microfuge spin, and cutting the adipocytes (thin layer of cells on top of the oil, buffer under oil) into LS vials with scintillation fluid. Glucose concentration was about 300 nM (sp.a. 295 mCi/mmol).

The effect of increasing concentrations of insulin in 30 μM D$^k$-(61-85) on glucose uptake was determined. Insulin induced maximally and 8-11 fold increase in glucose uptake as compared to basal uptake. Addition of D$^k$-(61-85) increased the maximal uptake to about 14-18 fold of basal, a glucose uptake above maximal insulin stimulation. At low concentrations of insulin (plasma level and lower), 30 μM D$^k$-(61-85) increased glucose uptake as much or more than insulin on a molar basis.

The maximal effect of D$^k$-(61-85) was obtained at 15 μM. It is found that the increase varies with the particular peptide batch, where the insulin effect of the peptide may vary from about 20% to 100%.

Various fragments of D$^k$-(61-85) were prepared by enzymatic digestion with specific peptidases: endo K, which gave fragments 61-68 and 69-85; endo E, which gave fragment 78-85; CP Y, which provided fragment 61-84; and in addition, the starting fragment was iodinated, which would be expected to occur at the terminal tyrosines. Each of the fragments were tested for biological activity after purification (greater than 95%) by HPLC and added to cells to a final concentration of 30 μM. The results reported as percent activity of the mean ±SE, with the starting fragment being 100 are as follows (61-68) 19±22; (69-85) 87±2; (78-85) 15±3; (61-84) 19±3; iodinated fragment 9±10.

The effect of $D^k$-(61-85) in whole rats was determined. $D^k$-(61-85) (2.5 mg/kg) and insulin (10 μg/kg) on the blood glucose levels in rats (100-300 g) was determined. The peptide and insulin were injected i.v. after the animals had been anesthetized with pentobarbital. All animals were starved 16-20 hrs. prior to experimentation. Each determination was based on results as obtained from 42 rats, where the same rats were used in the four treatment schedules. The schedules were a control, a peptide by itself, insulin by itself, and insulin plus peptide. The control showed no significant change in blood glucose over the 240 min. during which determinations were made. The peptide, at about 20 min., the blood glucose had dropped to about 65% of its original value and then slowly rose back to about the original value at about 90 min. and was maintained about the same level. A similar result was observed with the injection of insulin. However, where the insulin and peptide were injected together, the glucose dropped within about 20 min. to about 55% of its original value and slowly rose to about 85% of its original value at about 195 min. then gradually increase to about 90% at about 240 min. Calculation of the area between the control curve and the experimental curves from T=0 to T=240 showed that the area for insulin plus peptide is significantly larger than that of insulin or peptide alone, indicating a prolonged hypoglycemia period as compared to the insulin or peptide alone.

In order to determine the main target organs for peptide mediated glucose, the glucose uptake in various organs was analyzed as a function of olgopeptide injection i.v. The main target organs for peptide mediated glucose uptake are skeletal muscle, liver and kidney, when the size of the organ is considered. It is notable that some of these organs are not affected by insulin injection. The procedure employed was the injection of $^{14}$C-2-deoxyglucose 60 min. after injection of insulin plus peptide and the organ content of $^{14}$C measured 30 min. later, i.e. 90 min. after injection of peptide.

Based on the above data, it may be concluded that $D^k$-(61-85) peptide enhances cellular glucose uptake both in the absence and presence of insulin. Peptide effect is increased upon stimulation with insulin. Maximal peptide effect is reached at a peptide concentration of 10-20 μM. The peptide causes enhanced glucose uptake significantly above that induced by maximal insulin stimulation. The effect in vitro is maximal after 20 min. incubation of the cells with peptide. Intravenous injection of 2.5 mg/kg $D^k$-(61-85) peptide causes a decrease in blood glucose in whole animals. It is accentuated when insulin is injected together with the peptide. Glucose uptake as induced by peptide is particularly pronounced in muscle, liver and kidney, but the peptide does not result in increased levels of serum-insulin.

It is evident from the above results that high binding affinity proteins can be produced by combining a sequence which binds to the allosteric site of a surface membrane receptor to a sequence which binds to the ligand binding site of the receptor. In this way, when desired, one can either inhibit the functioning of the receptor or greatly enhance the activity of the receptor, by retaining the receptor in its activated form where a signal is continuously transduced. Furthermore, the allosteric binding peptide may affect one aspect of the transduced signal without affecting another, as is evidenced by the tyrosine kinase activity of the allosteric peptide in contrast with the glucose uptake activity. In addition, where other membrane receptors have similar sites, as has been observed with oncogenes, the same compounds used for controlling the membrane receptor may also be used to inhibit the action of the oncogene. A wide variety of physiological processes, both in vitro and in vivo, may be regulated by the subject products in view of their specificity and high binding affinity.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A composition of matter comprising a polypeptide sequence of a polymorphic region of a Class I major histocompatibility complex antigen, wherein said polypeptide sequence consists essentially of at least 8 amino acids in sequence of the sequence E-R-E-T-Q-I-A-K-G-N-E-Q-S-F-R-V-D-K-R-T-K-K-R-Y-Y, wherein said at least about 8 amino acid sequence has R-Y or R-Y-Y at the C-terminus and which binds to other than the ligand binding site of a mammalian naturally occurring surface membrane receptor, wherein aid receptor is for insulin or epidermal growth factor, wherein said binding results in a change in conformation of said receptor, said polypeptide sequence joined covalently to a compound which binds to the binding site of said receptor.

2. A composition according to claim 1, wherein said composition is a polypeptide, said compound and said polypeptide sequence being joined by a bond or an amino acid bridge of from 1 to 20 amino acids.

3. A composition of matter comprising a polypeptide sequence of a polymorphic region of a Class I major histocompatibility complex antigen, wherein said sequence consists essentially to at least 8 amino acids in sequence of the sequence E-R-E-T-Q-I-A-K-G-N-E-Q-S-F-R-V-D-L-R-T-L-R-Y-Y, wherein the C-terminus is R-Y or R-Y-Y and, which binds at other than the ligand binding site to a insulin receptor, wherein said binding results in a change in conformation of said receptor, said polypeptide sequence joined covalently to a polypeptide sequence of the A-chain of insulin which binds to the binding site of the insulin receptor.

4. A composition according to claim 3, wherein said major histocompatibility complex antigen polypeptide is joined to said polypeptide sequence of the A-chain of insulin by a bond or an amino acid bridge of from 1 to 20 amino acids.

5. A method for enhancing glucose uptake in a mammalian cell comprising a functional insulin receptor, said method comprising: combining said cell with a composition of matter comprising a polypeptide sequence of a polymorphic region of a Class I major histocompatibility complex antigen of at least 8 amino acids in sequence of the sequence E-R-E-T-Q-I-A-K-G-N-E-Q-S-F-R-V-D-L-R-T-L-L-R-Y-Y, and terminating in R-Y or R-Y-Y and which binds at other than the ligand bindign site to a insulin receptor, said polypeptide sequence joined covalently to at least a segment of the A-chain of insulin which binds to the binding site of the insulin receptor and glucose in a nutrient medium; wherein glucose uptake is enhanced.

6. A formulation comprising a composition of matter according to claim 1 in an amount sufficient to bind to said receptor in a physiologically acceptable medium.

* * * * *